(12) United States Patent
Solomon et al.

(10) Patent No.: US 6,488,664 B1
(45) Date of Patent: Dec. 3, 2002

(54) EASILY RELEASABLE CLAMP

(75) Inventors: Rodney J. Solomon, Andover, MA (US); Roger A. Dugas, Chester, NH (US)

(73) Assignee: Koninklijke Phillips Electronics, Eindhoven (NL)

( * ) Notice: Subject to any disclaimer, the term of this patent is extended or adjusted under 35 U.S.C. 154(b) by 167 days.

(21) Appl. No.: 09/627,467

(22) Filed: Jul. 28, 2000

(51) Int. Cl.$^7$ ................................................ A61M 5/32
(52) U.S. Cl. .......................... 604/174; 604/178; 602/17; 24/20 R
(58) Field of Search ............................ 602/17; 604/174, 604/178; 24/20 R, 20 TT, 20 CW, 270, 275; 285/242, 921

(56) References Cited

U.S. PATENT DOCUMENTS

| | | |
|---|---|---|
| 1,441,154 A | 1/1923 | Johnson |
| 1,579,719 A | 4/1926 | Lavender |
| 2,374,541 A | 4/1945 | Hartman |
| 4,183,120 A | 1/1980 | Thorne |
| 4,306,740 A | 12/1981 | Kleykamp et al. |
| 4,483,556 A | 11/1984 | LiVolsi |
| 4,502,186 A | 3/1985 | Clarke et al. |
| 4,511,164 A | 4/1985 | Orchard |
| 4,663,807 A | 5/1987 | Bozzo |
| 4,986,815 A * | 1/1991 | Schneider .................... 604/180 |
| 5,157,815 A | 10/1992 | Dyer |
| 5,185,005 A * | 2/1993 | Ballantyne .................. 604/174 |
| 5,533,506 A * | 7/1996 | Wood ..................... 128/207.18 |
| 5,681,290 A | 10/1997 | Alexander |
| 5,687,455 A | 11/1997 | Alexander |
| 5,836,054 A | 11/1998 | Alexander |

\* cited by examiner

*Primary Examiner*—Thomas Denion
*Assistant Examiner*—Jaime Corrigan

(57) ABSTRACT

A clamp for a tube having particular application to a nose trumpet for use with a transnasal TEE probe. The clamp includes a generally circular band for encircling the tube and a tongue disposed on one end of the band and a pair of jaws disposed on the other end. The tongue is adapted to penetrate the space between the pair of jaws. Teeth disposed on the upper surface of the tongue are adapted to mesh with teeth disposed on the lower surface of the upper jaw to prevent withdrawal of the tongue. A pair of handles extend outwardly away from the interior of the band and are adapted to be pushed toward one another to cause penetration of the tongue and into the jaws. An arm hinged to the band is affixed to the upper jaw and upon pivoting of the arm, the upper jaw is lifted away from the tongue to disengage the teeth.

12 Claims, 3 Drawing Sheets

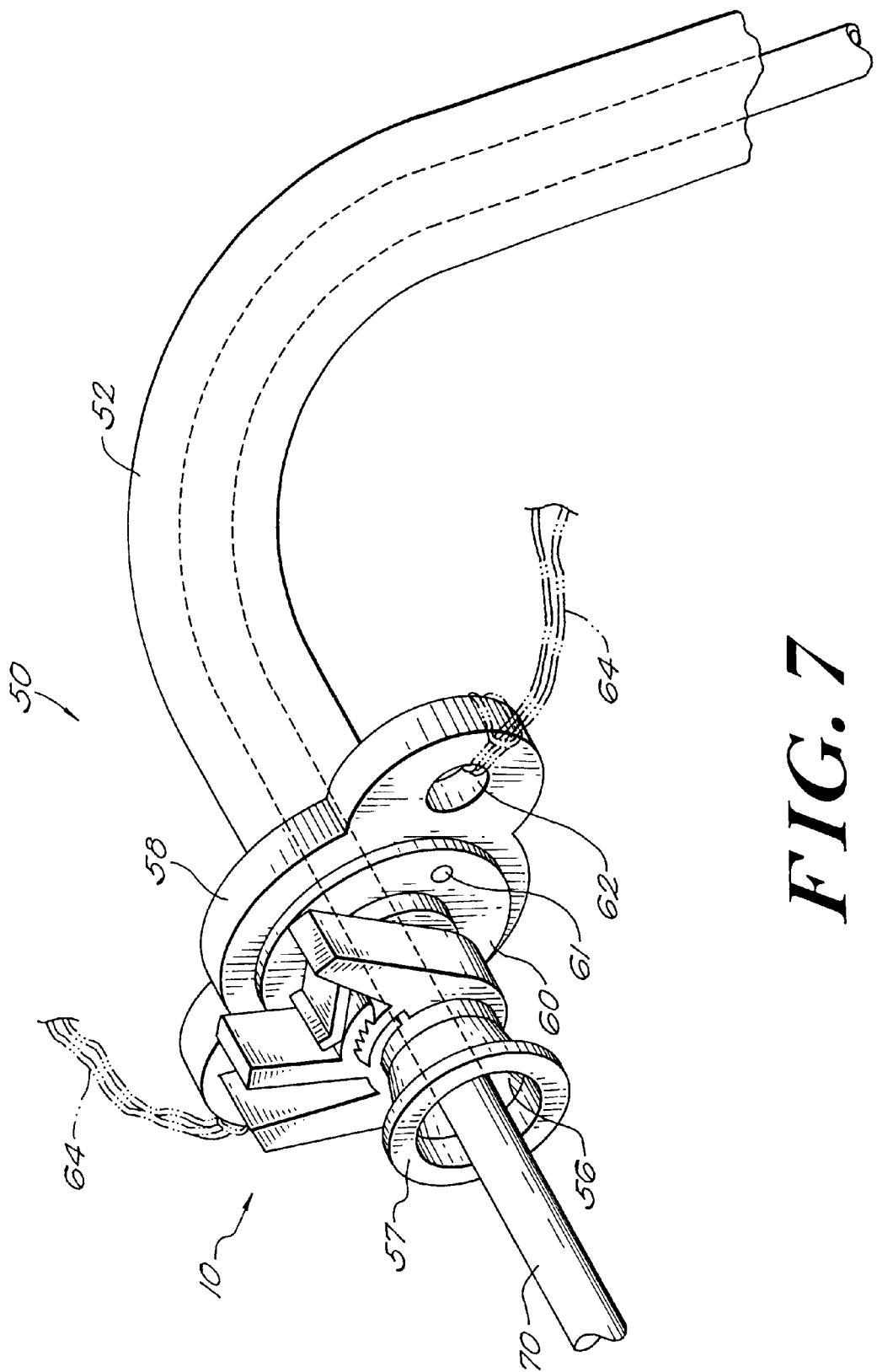

EASILY RELEASABLE CLAMP

FIELD OF THE INVENTION

This invention relates generally to hose or tube clamps, and more particularly to an easily releasable clamp having medical applications.

BACKGROUND OF THE INVENTION

Clamps for flexible tubes or hoses are well-known and are widely used throughout medicine and industry. Many of such clamps include an adjustable band which is adapted to be disposed around an associated tube or hose end to clamp the tube or hose end around an associated structure, such as a tubular connector or the like.

Various types of prior art hose or tube clamps include a band equipped with fittings of various kinds including worm drive devices and single ratchet-type dog-tooth devices for contracting the band to tighten it and clamp the band about a hose or tube which it encircles. These types of prior art clamps suffer disadvantages of one sort or another including being difficult or time consuming to apply, being unreliable in service, being insufficiently strong to sustain the pressures to which the hose or tube and the clamp may be subjected in use, being expensive to manufacture or becoming unserviceable after use. Other types of prior art clamps include an integral helical wire in which the clamp uses an over-center toggle link connected to the helical wire.

Another well-known type of hose or tube clamp includes a pair of cooperating interconnectable jaws, each having a plurality of serrations or teeth adapted for interconnecting engagement. Typically, the teeth are angled such that pushing the jaws toward one another is permitted and tightens the clamp, while the angle of the teeth prevents the jaws from being pulled away from one another to loosen the clamp. These clamps using serrated jaws are often very difficult to loosen, because of the angular orientation of the teeth. In one type of device, such as that shown in U.S. Pat. No. 4,306,740, a screwdriver is required to lift a lever for release and this mechanism requires the application of considerable force. In another embodiment, such as that shown in U.S. Pat. Nos. 4,502,186 and 4,663,807, lateral movement of one jaw with respect to another is required for release, thus distorting the clamp. Other clamps require the lifting of a handle for release which results in the application of force to the clamp or to the hose or tube being encircled by the clamp.

Examples of these clamps are found in U.S. Pat. Nos. 5,157,815; 1,579,719; 1,441,154; and 4,511,164.

None of the foregoing prior art clamps is particularly suitable for medical applications in which secure clamping is desired, but in which it may be undesirable to apply a force to the clamp or tube or hose during removal of the clamp. The application of such a force could damage or break the tube or connector which is being clamped if it is either fragile or easily damaged. Moreover, the application of such a force could cause discomfort or injury to the patient.

A nasal trumpet is one application in which a clamp is desired that can be easily applied and removed without the use of a tool and without the application of a force to the portion of the clamp which encircles the tube or hose. A nasal trumpet is a device that acts as a guide into the nasal passage of a patient to allow easier and more comfortable insertion of a transnasal transesophageal echocardiography (TEE) probe. The nasal trumpet includes a tube formed of a soft, elastomeric material which passes through and is bonded to a support structure for the tube. The support structure in turn is firmly attached to the patient's head. Typically, the distal end of the tube is inserted into the patient's nasal passage and the proximal end is secured and supported by the support structure. One device used to secure the support structure to the patient's head is an elastic band which extends around the back of the patient's head and which is attached to the support structure. The distal 30–40 cm of the transnasal TEE probe is inserted into the proximal end of the tube that extends from the support structure and that protrudes slightly from the patient's nose.

Presently, there is no suitable clamp available for securing the trumpet to the transnasal TEE probe. Such a clamp should be capable of providing sufficient clamping force to prevent movement of the probe with respect to the nasal trumpet without damaging the insertion tube of the probe. Such a clamp should also be easy to apply and release without causing injury or discomfort to the patient, and should be capable of accommodating variations in size of the trumpet and insertion tube.

SUMMARY OF THE INVENTION

The present invention relates to a tube clamp that overcomes the disadvantages of prior art clamps and that meets the needs of a transnasal TEE probe and nasal trumpet assembly. In one aspect, the tube clamp of the present invention includes a band formed in an open-ended band or loop for encircling the tube. One end of the band terminates in a pair of jaws, while the opposite end of the band terminates in a tongue which is structured to extend between the pair of jaws. The tongue contains a set of serrations or angled teeth on its upper surface which are adapted to mesh with facing, confronting serrations or angled teeth disposed on the lower surface of the upper jaw of the other end of the loop.

In a further aspect, the clamp includes an arm extending outwardly away from the encircling band of the clamp. The arm is affixed to the upper jaw and is pivotable about a hinge section. Pivoting of the arm about its hinge raises the upper jaw away from the tongue to disengage the serrations from one another to permit loosening of the clamp.

In another aspect, the serrations are angled such that movement of the tongue into the jaw is permitted, but withdrawal of the tongue from between the jaws is prevented by interlocking of the serrations on the tongue with the serrations on the upper jaw. The tongue preferably has a spring bias that urges it toward the upper jaw.

In another further aspect, the clamp also includes two spaced handles. A leaf spring may also be provided on one of the two handles and the spring engages the top surface of the upper jaw to urge the upper jaw toward the tongue to urge the serrations on the upper jaw into engagement with the serrations on the upper surface of the tongue. This leaf spring is permitted to flex upwardly away from the upper jaw in response to pivoting of the arm about the hinge to raise the upper jaw. Clamping of a tube is accomplished by squeezing the two handles toward one another to urge the tongue between the jaws until the desired clamping force is obtained. If the arm and the other of the two handles are squeezed together, or if the two handles are moved away from one another, the arm is caused to pivot about its hinge to raise the upper jaw away from the tongue to permit loosening of the clamp. Preferably, the clamp is a one-piece clamp formed of a molded polymeric material.

When the above clamp is used with a transnasal TEE probe, the tube of the trumpet is inserted into the nasal passage of the patient. The support for the tube is affixed to the patient's head using an elastic band or the like. The outer portion of the proximal end of the tube already contains the clamp loosely positioned. The distal end of the tube is inserted down the nasal passage and into the esophagus of the patient. The transnasal TEE probe is then inserted into the proximal end of the tube of the trumpet until it is in the desired position. At that point, the first and second handles of the clamp are squeezed together to urge the tongue between the jaws until the desired clamping force about the probe tube has been achieved. When the examination is complete, the clamp is removed by squeezing together the first handle and the arm to pivot the upper jaw upwardly away from the tongue to disengage the serrations to permit the first and second handles to be pulled apart to loosen the clamp. The foregoing structure permits the clamp to be readily applied and removed without excessive force on the tube or hose being clamped, or on a patient. The clamp need not be cut or distorted for removal, and no tool is required. These features are particularly important for use in conjunction with a nose trumpet.

BRIEF DESCRIPTION OF THE DRAWINGS

The objects, advantages and features of this invention will be more clearly appreciated from the following detailed description, when taken in conjunction with the accompanying drawings, in which:

FIG. 7 is a perspective view of the clamp of this invention when used with a nasal trumpet assembly.

DETAILED DESCRIPTION

Figure 1:
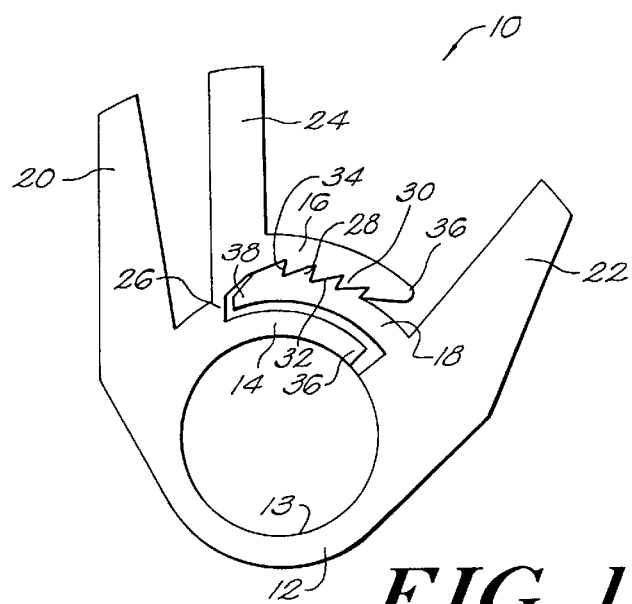
FIG. 1 is a front, elevational view of the clamp of this invention.

With reference now to the drawings, and more particularly to FIG. 1 thereof, the clamp 10 of this invention will be described. Clamp 10 includes a generally circular band or loop 12 for encircling a tube or the like, a pair of opposed jaws, lower jaw 14 and upper jaw 16, extending from one end of band 12 and a tongue 18 extending from the other end of band 12. Jaws 14 and 16 have distal ends 36, while tongue 18 has a distal end 38. Distal end 38 and distal end 36 of jaw 16 preferably are tapered. Clamp 10 also includes two opposed outer handles, 20 and 22 and a pivotally mounted release arm 24 disposed between handles 20 and 22.

Handles 20 and 22 extend outwardly away from band 12 and preferably are either generally parallel to one another or form an obtuse angle with respect to one another. Handles 20 and 22 are relatively rigidly affixed to band 12, and do not pivot with respect to the band. In this way, if handles 20 and 22 are urged toward one another, tongue 18 is urged into the space between jaws 14 and 16, as will be described. Handles 20 and 22 are preferably spaced sufficiently closely that an operator can apply a thumb to one handle and a forefinger to the other to squeeze the handles together. However, handles 20 and 22 are spaced sufficiently distant from one another that squeezing the handles together permits the clamp 10 to close completely about a tube.

Release arm 24 is coupled to band 12 by a narrow hinge 26, which also joins upper jaw 16 to lower jaw 14. Upper jaw 16 extends from release arm 24 at an angle that is generally perpendicular thereto. Lower jaw 14 is substantially parallel to upper jaw 16 and is disposed below hinge 26. Movement of arm 24 toward or away from handle 20 about hinge 26 causes upper jaw 16 to pivot upwardly or downwardly, respectively, away from or toward tongue 18, respectively, substantially independently of jaw 14.

Disposed on an upper surface of tongue 18 confronting a lower surface of jaw 16 are a plurality of serrations or teeth 28. Teeth 28 are angled toward handle 22 and away from release arm 24 and handle 20. Similarly, disposed on the lower surface of jaw 16 are a plurality of serrations or teeth 30 which are adapted to mate with teeth 28, and which are angled toward release arm 24 and handle 20. Teeth 28 and 30 each include longer surfaces 32 which are somewhat parallel to an inner surface 13 of band 12 and which intersect with shorter surfaces 34 disposed at an acute angle with respect to surfaces 32. Surfaces 34 on both teeth 28 and 30 are disposed at an angle with respect to the interior surface 13 of band 12, and, in one embodiment, are substantially parallel to a radius of band 12. Surfaces 34 on teeth 28 are generally parallel to surfaces 34 on teeth 30, while surfaces 32 on teeth 28 are also generally parallel to surfaces 32 on teeth 30.

As a result of the orientation of teeth 30 and 28, as tongue 18 is inserted between jaws 14 and 16, respective surfaces 32 on teeth 28 and 30 slide freely over one another allowing tongue 18 to penetrate between jaws 14 and 16. However, if one tries to withdraw tongue 18 from between jaws 14 and 16, surfaces 34 on teeth 28 and 30 come into abutting engagement with one another preventing withdrawal of tongue 18 from between jaws 14 and 16.

Beneath tongue 18 is a recess in band 12 configured to accommodate jaw 14, so that the lower surface of jaw 14 is substantially coextensive with the interior surface 13 of band 12. In this way, pressure is applied uniformly around the circumference of a tube, and not just at certain portions thereof.

Figure 2:
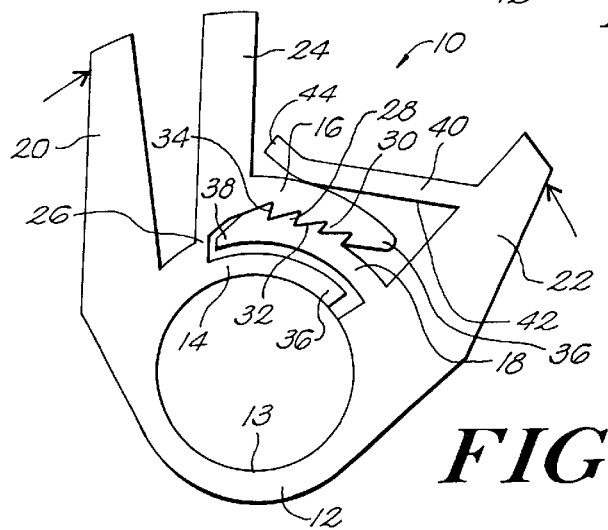
FIG. 2 is a front, elevational view of another embodiment of the clamp of FIG. 1.

In one embodiment of the clamp of this invention, as shown in FIG. 2, a leaf spring 40 may be provided which extends from handle 22 toward release arm 24. Like numbers are used for like parts in FIG. 1, where appropriate. Spring 40 is configured so that it is biased downwardly toward upper jaw 16 so that a lower surface 42 of spring 40 rests on an upper surface of jaw 16 and urges jaw 16 downwardly toward tongue 18. Spring 40 ensures a secure engagement of teeth 28 by teeth 30 when it is desired to tightly apply the clamp to a tube. However, spring 40 is sufficiently flexible that when release arm 24 is pivoted about hinge 26, upper jaw 16 is permitted to rise upwardly away from tongue 18 and overcome the downward force applied by spring 40. Thus, spring 40 typically is more flexible than jaw 16. The tip 44 of spring 40 may be angled upwardly away from jaw 16 to facilitate movement of jaw 16 away from tongue 18, although tip 44 need not be angled upwardly. Tip 44 should be spaced from release arm 24 sufficiently so as not to interfere with the movement of release arm 24 so as not to prevent clamp 10 from closing, and so as not to prevent release arm 24 from returning to its home position to insure secure engagement between teeth 28 and 30.

Figure 3:
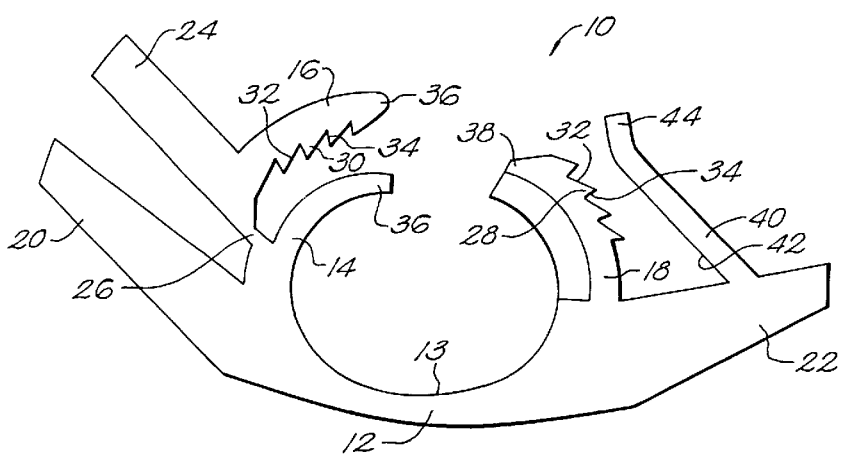
FIG. 3 is a front, elevational view of the clamp of FIG. 2 in an open position.
Figure 4:
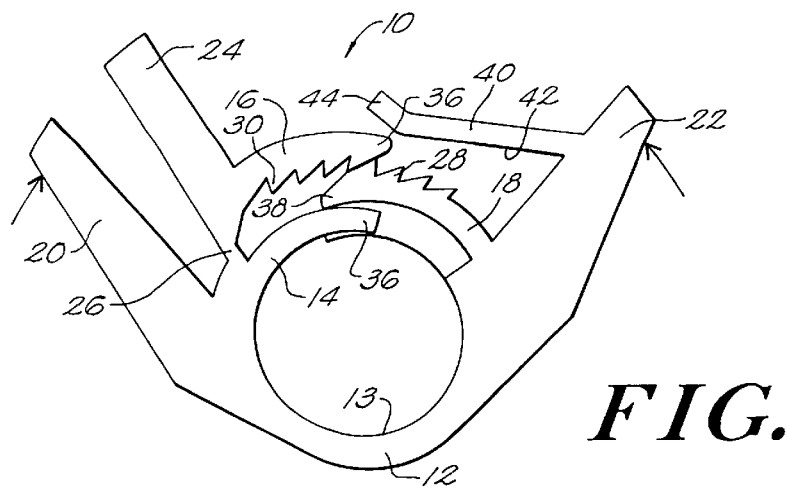
FIG. 4 is a front, elevational view of the clamp of FIG. 2 illustrating the clamping operation.
Figure 5:
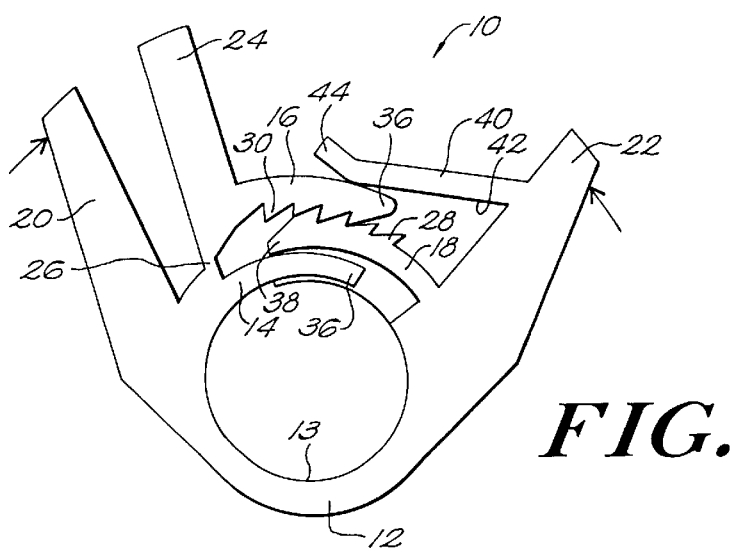
FIG. 5 is a front, elevational view illustrating the clamp of this invention in a partially closed position.

Operation of the clamp of this invention will now be described with particular reference to FIGS. 2–6. Like numbers are used for like parts in these figures, where applicable. Initially, tongue 18 is sufficiently withdrawn from between jaws 14 and 16 that teeth 28 do not engage teeth 30. This arrangement permits the user to grasp handles 20 and 22 and pull them apart sufficiently, as shown in FIG. 3, to insert a tube into the clamp 10 between the distal end 38 of tongue 18 and the distal ends 36 of jaws 14 and 16. Thereafter, once band 12 encircles a tube, the user grasps handles 20 and 22, preferably with one hand, and begins squeezing them together, as shown in FIG. 4. Typically, the user applies a thumb to one of handles 20 and 22 and a forefinger to the other of handles 20 and 22. The tapered distal end 36 of jaw 16 and the tapered distal end 38 of tongue 18 facilitate the passage of distal end 38 past the opening between jaws 14 and 16, as shown in FIG. 5. Continued pressure applied to handles 20 and 22 toward one another causes tongue 18 to penetrate into the space between jaws 14 and 16, as shown in FIG. 5. Once the desired clamping pressure has been applied, the user releases the squeezing force on handles 20 and 22. At this point, the somewhat compressed tube is exerting a radially outwardly directed force that attempts to expand band 14 and separate tongue 18 from jaws 14 and 16. This force causes surfaces 34 on teeth 28 and 30 to engage one another to interlock teeth 28 and 30.

Figure 6:
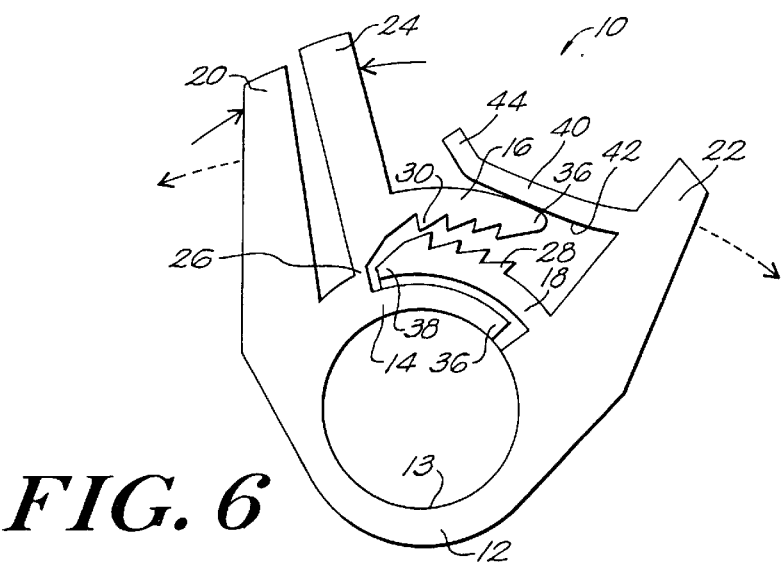
FIG. 6 is a front, elevational view of the clamp of this invention illustrating the process of opening the clamp.

When it is desired to remove clamp 10, the user applies a force urging handle 20 and arm 24 together, typically using the thumb and forefinger. This force causes arm 24 to pivot about hinge 26 toward handle 20, which in turn raises jaw 16 upwardly away from jaw 14 and away from tongue 18. The user continues to apply the force until surfaces 34 become disengaged and the teeth 28 and 30 are no longer interlocking, as shown in FIG. 6. At this point, the user may then apply a force to handle 22 away from handle 20 to open the clamp and withdraw tongue 18 from between jaws 14 and 16 to the position shown in FIG. 4. Thereafter, the user may release arm 24 and continue applying a force urging handles 20 and 22 away from each other until the spacing between distal ends 36 and 38 is sufficient to allow the tube to pass therebetween, as shown in FIG. 3, or until the clamping force applied to the tube is sufficiently reduced that a tube or probe within the tube may be axially withdrawn from the clamp.

The use of clamp 10 in conjunction with a nasal trumpet assembly 50 and a nasal TEE probe (not shown) will now be described with particular reference to FIG. 7. Like numbers are used for like parts where applicable. Nasal trumpet assembly 50 includes a tube 52 and a flange 58. Tube 52 typically is formed of a soft elastomeric material adapted to extend through the nasal passage of the patient and down into the esophagus. Tube 52 is adapted to receive a TEE probe tube 70 which extends therethrough. The proximal end 57 of tube 52 protrudes from the nose of the patient. Flange 58 is attached to a proximal section of tube 52 by a mounting collar 60. Collar 60 is in a tight, friction fit with the exterior surface of the proximal end of tube 52 to prevent movement of tube 52 with respect to collar 60. Collar 60 is in turn attached to flange 58 by pegs 61 or the like. The proximal end 57 of tube 52 has an opening 56 through which the TEE probe tube is inserted. Typically, although not necessarily, the proximal end 57 of tube 52 is flared, as shown. A strap 64 is affixed to flange 58 at openings 62 disposed on either side of collar 60 and is constructed to extend around the back of the patient's head to hold trumpet assembly 50 tightly on the patient's head and to prevent any movement thereof with respect to the patient. Typically, strap 64 is elastomeric, although it need not be. Clamp 10 is disposed between the proximal end 57 of tube 52 and flange 58.

The use of clamp 10 of this invention in conjunction with trumpet assembly 50 will now be described with particular reference to FIGS. 4, 6 and 7. Tube 52 is provided with flange 58 attached thereto adjacent proximal end 57. Enough space is provided between flange 58 and proximal end 57 to permit mounting of clamp 10. Clamp 10 may be either loosely disposed between flange 58 and proximal end 57, or it may be mounted at a later time. The distal end of tube 52 is inserted through the nasal passage of the patient to extend downwardly into the esophagus. The insertion process is continued until flange 58 either abuts or is closely spaced from the nose of the patient. Strap 64 is looped around the back of the patient's head to hold flange 58 and thus proximal end 57 of tube 52 in place with respect to the patient.

Thereafter, with clamp 10 either removed, or in a loosely clamped position about tube 52, TEE probe tube 70 is inserted into tube 52 through the proximal end 57. When the probe tube 70 is in its desired position within tube 52, either clamp 10 is mounted onto tube 52 between proximal end 57 and flange 58 and tightened, or the previously placed clamp 10 is tightened. In either event, the operator grasps handles 20 and 22 of clamp 10 and urges them together, to insert tongue 18 between jaws 14 and 16, as previously described. When the desired clamping force on tube 52 has been applied, the operator releases his or her fingers. Clamp 10 tightly secures tube 52 to the TEE probe tube 70 to prevent movement of the TEE probe tube 70 with respect to the patient during an examination. A total lack of movement is very important to the ability to obtain a good image during the ultrasound examination.

Clamp 10 provides a uniform compression load around the circumference of tube 52 to prevent movement of the probe tube 70 with respect to tube 52. However, the force applied is not sufficiently great that either probe tube 70 or tube 52 is damaged. Moreover, because of the adjustable nature of the clamp 10, different sized probe tubes 70 and different diameter tubes 52 may be accommodated with one size clamp.

When the examination is complete, clamp 10 may be removed as previously described. The operator urges release arm 24 toward handle 20, causing upper jaw 16 to rise upwardly away from tongue 18 so that teeth 28 and 30 disengage. Once teeth 28 and 30 have become disengaged, the operator opens clamp 10 by grasping handles 20 and 22 and moving them apart from one another until sufficient pressure has been released to allow withdrawal of the TEE probe tube 70 from tube 52. Thereafter, strap 64 is disengaged from the patient's head and the trumpet assembly 50 including tube 52, is withdrawn from the patient's nose. Clamp 10 permits release and disengagement without applying any force to tube 52 or to the TEE probe tube 70 which could cause damage to the probe. Also, no force is applied to the nose of the patient or to other portions of the body which would be painful or irritating to the patient. The release process is simple, straightforward and can be accomplished in a matter of seconds.

Preferably, clamp 10 is formed of a molded, unitary piece. However, it is possible to assemble clamp 10 from various components, so long as the desired result is achieved. Typically, clamp 10 formed of a polymeric material, such as a synthetic plastic material, which is capable of being injection molded and which has the necessary flexibility and resiliency. An example of an acceptable material is Polyamide (Nylon) or Polyethylene.

Modifications and improvements will occur within the scope of this invention to those skilled in the art, and the above description is intended to be exemplary only. The scope of this invention is defined only by the following claims and their equivalents.

What is claimed is:

1. A device for clamping comprising:
    a circular band having an interior;
    a pair of spaced jaws disposed on one end of the band and including an upper jaw and a lower jaw, the lower jaw being disposed between the upper jaw and the interior of the band, the upper jaw having a distal end and an end opposite the distal end;
    angled teeth disposed on a lower surface of the upper jaw facing the interior of the band;
    a tongue disposed on an other end of the band and adapted to be inserted between the pair of jaws;
    angled teeth disposed on an upper surface of the tongue for meshing with the angled teeth disposed on the lower surface of the upper jaw;
    an arm extending outwardly away from the interior of the band, the arm being connected to the upper jaw near the end opposite the distal end; and
    a hinge connecting the arm to the band to allow pivoting of the arm with respect to the band and pivoting of the upper jaw with respect to the lower jaw.

2. The device as recited in claim 1 further comprising a spring for urging the upper jaw toward the lower jaw.

3. The device as recited in claim 1 wherein the teeth on the lower surface of the upper jaw have substantially the same size and shape as the teeth disposed on the upper surface of the tongue.

4. The device as recited in claim 1 wherein the teeth on the lower surface of the upper jaw and on the upper surface of the tongue are angled such that the tongue can move between the jaws toward the jaws and wherein withdrawal of the tongue from between the jaws causes the teeth on the lower surface of the upper jaw and on the upper surface of the tongue to engage one another.

5. The device as recited in claim 1 wherein pivoting of the arm about the hinge in one direction causes the upper jaw to rise off the tongue to permit disengagement of the teeth disposed on the lower surface of the upper jaw from the teeth on the upper surface of the tongue.

6. The device as recited in claim 5 wherein pivoting of the arm about the hinge in another direction causes the upper jaw to move toward the tongue to permit meshing of the teeth on the upper surface of the tongue with the teeth on the lower surface of the upper jaw.

7. The device as recited in claim 1 further comprising a pair of spaced handles extending from the band away from the interior thereof and wherein a force applied to the handles toward one another urges the tongue between the two jaws.

8. The device as recited in claim 7 wherein movement of the handles away from one another withdraws the tongue from between the pair of jaws after pivoting of the upper jaw away from the lower jaw.

9. The device as recited in claim 1 where the band, the tongue, the jaws, the arm and the hinge are formed as a single piece.

10. A nose trumpet assembly comprising:
    a length of tubing having a distal end and a proximal end, the proximal end having an opening;
    a flange attached to the tubing and disposed adjacent but spaced from the proximal end of the tubing; and
    a clamp disposed between the proximal end of the tubing and the flange, the clamp comprising:
        a band for encircling the tube;
        a pair of jaws disposed on one end of the band, the pair of jaws including an upper jaw and a lower jaw;
        a tongue disposed on another end of the band and constructed to be inserted between the pair of jaws;
        teeth disposed on opposed, confronting surfaces of the tongue and the upper jaw for preventing movement of the tongue with respect to the pair of jaws in a direction away from the pair of jaws;
        an arm mounted onto the band and coupled to the upper jaw;
        a hinge permitting the arm to pivot with respect to the band to raise the upper jaw away from the tongue to disengage the teeth on the tongue from the teeth on the upper jaw; and
        an elastic band attached to the flange and constructed to encircle a head of a patient.

11. The nose trumpet assembly as recited in claim 10 further comprising a pair of spaced handles extending outwardly away from the band of the clamp, the tongue being urged between the pair of jaws when the handles are moved toward one another.

12. The nose trumpet assembly as recited in claim 10 further comprising a spring for urging the upper jaw toward the tongue of the band.

* * * * *

UNITED STATES PATENT AND TRADEMARK OFFICE
CERTIFICATE OF CORRECTION

PATENT NO. : 6,488,664 B1
DATED : December 3, 2002
INVENTOR(S) : Rodney J. Solomon and Roger A. Dugas It is certified that error appears in the above-identified patent and that said Letters Patent is hereby corrected as shown below:

<u>Title page,</u>
Item [73], Assignee, change "Phillips" to -- Philips --.

Signed and Sealed this

First Day of April, 2003

JAMES E. ROGAN
*Director of the United States Patent and Trademark Office*